(12) United States Patent
Tsuji

(10) Patent No.: US 7,485,736 B2
(45) Date of Patent: Feb. 3, 2009

(54) PROCESS FOR PRODUCING α-METHYLSTYRENE

(75) Inventor: Junpei Tsuji, Chiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 317 days.

(21) Appl. No.: 10/573,010

(22) PCT Filed: Sep. 10, 2004

(86) PCT No.: PCT/JP2004/013588

§ 371 (c)(1), (2), (4) Date: Mar. 22, 2006

(87) PCT Pub. No.: WO2005/030684

PCT Pub. Date: Apr. 7, 2005

(65) Prior Publication Data

US 2007/0043227 A1    Feb. 22, 2007

(30) Foreign Application Priority Data

Sep. 25, 2003    (JP) .............................. 2003-333145

(51) Int. Cl.
*C07D 301/02* (2006.01)
*C07D 301/19* (2006.01)
(52) U.S. Cl. ...................... 549/518; 549/529
(58) Field of Classification Search ............... 585/440, 585/437; 549/518, 529
See application file for complete search history.

(56) References Cited

U.S. PATENT DOCUMENTS 3,526,674 A * 9/1970 Becker et al. ............... 585/437
7,319,177 B2 * 1/2008 Tsuji et al. ................. 585/440

* cited by examiner

*Primary Examiner*—Taylor Victor Oh
(74) *Attorney, Agent, or Firm*—Sughrue Mion, PLLC

(57) ABSTRACT

A process for producing α-methylstyrene from cumyl alcohol via dehydration in the presence of activated alumina, wherein a concentration of propylene oxide contained in a raw material containing cumyl alcohol is 10 to 1000 ppm by weight.

2 Claims, No Drawings

PROCESS FOR PRODUCING α-METHYLSTYRENE

TECHNICAL FIELD

The present invention relates to a process for producing α-methylstyrene. More particularly, the present invention relates to a process for producing α-methylstyrene, which can effectively attain high conversion of cumyl alcohol at low cost.

BACKGROUND ART

There is publicly known a process for producing α-methylstyrene by dehydrating cumyl alcohol in the presence of activated alumina (e.g. U.S. Pat. No. 3,403,193). However, the conventional technique could not be necessarily satisfied from the viewpoint of efficient attainment of high conversion of cumyl alcohol at low cost because it required considerably high temperature for attaining high conversion.

DISCLOSURE OF THE INVENTION

An object of the present invention is to provide a process for producing α-methyl styrene, which can efficiently attain high conversion of cumyl alcohol at low cost.

Namely, the present invention relates to a process for producing α-methylstyrene, which comprises dehydrating cumyl alcohol in the presence of activated alumina, wherein a concentration of propylene oxide contained in a raw material containing cumyl alcohol is 0 to 10,000 ppm by weight.

MODE FOR CARRYING OUT THE INVENTION

The dehydration is usually carried out by contacting cumyl alcohol with activated alumina as a dehydration catalyst. The reaction can be carried out in a gas phase or a liquid phase using a solvent. The reaction is preferably carried out in a liquid phase from the viewpoint of productivity and energy saving. The solvent should be substantially inert to reactants and products. The solvent may be a substance present in a cumyl alcohol solution to be used. For example, when cumyl alcohol is a mixture with cumene as a product, it is possible to use cumene as a substitute without adding a solvent in particular. As other useful solvents, there can be listed alkanes (e.g. octane, decane, dodecane), mono-cyclic aromatic compounds (e.g. benzene, ethylbenzene, toluene) and the like. The dehydration temperature is usually 50 to 450° C., and preferably 150 to 300° C. In usual, the pressure is advantageously 10 to 10,000 kPa. When the equilibrium of the reaction is considered, it is advantageous that the pressure is set up as low as possible. The dehydration can be advantageously carried out by using a catalyst in the form of a slurry or fixed-bed.

The feature of the present invention is to carry out the reaction in the presence of activated alumina with controlling propylene oxide contained in the raw material containing cumyl alcohol to 0 to 10,000 ppm by weight. The concentration of propylene oxide in the raw material is preferably 0 to 5000 ppm by weight.

When the amount of propylene oxide in the raw material containing cumyl alcohol is over the above-described range, a catalyst activity of the activated alumina deteriorates, therefore, it is necessary to rise the reaction temperature to adjust a conversion of cumyl alcohol to a satisfied range, and it leads to disadvantage from viewpoints of energy and yield.

The process of the present invention can be suitably applied to a dehydration step in production process of propylene oxide described below:

oxidation step: a step of obtaining cumene hydroperoxide by oxidizing cumene;

epoxidation step: a step of obtaining propylene oxide and cumyl alcohol by reacting cumene hydroperoxide contained in a cumene solution with propylene in an excess amount in the presence of a solid catalyst in a liquid phase;

dehydration step: a step of obtaining α-methylstyrene by dehydrating cumyl alcohol obtained in the epoxidation step in the presence of a dehydration catalyst; and hydrogenation step: a step of converting α-methylstyrene into cumene in the presence of a hydrogenation catalyst and recycling the cumene to the oxidation.

The oxidation of cumene in the oxidation step is usually conducted by auto-oxidation using an oxygen-containing gas such as air or oxygen-concentrated air. This oxidation may be conducted without use of an additive, or an additive such as an alkali may be used. The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, an alkali metal carbonate such as $Na_2CO_3$ or $NaHCO_3$, ammonia, $(NH_4)_2CO_3$, an alkali metal ammonium carbonate or the like, is used as the alkali reagent.

As a catalyst used in the epoxidation step, a solid catalyst containing a titanium-containing silicon oxide is preferable from the viewpoint of obtaining the objective product under high yield and high selectivity. As the catalyst, a so-called Ti-silica catalyst containing Ti chemically bonded to silicon oxide, is preferable. For example, a catalyst prepared by supporting a Ti compound on a silica carrier, a catalyst prepared by combining a Ti compound with silicon oxide by a co-precipitation method or sol gel method, zeolite compounds containing Ti, and the like, can be listed.

Cumene hydroperoxide used as the raw material in the epoxidation step, may be a dilute or dense purified material or non-purified material.

The epoxidation is carried out by contacting propylene and cumene hydroperoxide with the catalyst. The reaction is carried out in a liquid phase using a solvent. The solvent should be liquid under a temperature and pressure in the reaction, and substantially inert to the reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent. Additionally, mono-cyclic aromatic compounds (e.g. benzene, toluene, chlorobenzene, orthodichlorobenzene), alkanes (e.g. octane, decane, dodecane) and the like, can be listed as useful solvents.

The epoxidation temperature is usually from 0 to 200° C., and preferably from 25 to 200° C. The pressure may be a pressure enough to keep the reaction mixture in a liquid condition. In general, the pressure is advantageously from 100 to 10,000 kPa.

The catalyst can be advantageously used in the form of a slurry or fixed bed. In a case of a large-scale industrial operation, a fixed bed is preferably used. In addition, the epoxidation can be conducted by a batch-wise method, semi-continuous method or continuous method.

The molar ratio of propylene to cumene hydroperoxide supplied to the epoxidation step, is preferably 2/1 to 50/1.

When the ratio is smaller than 2/1, the efficiency may be deteriorated by lowering of the reaction rate, on the other hand, when the ratio is larger than 50/1, large energy in the recycling step is required because the amount of propylene to be recycled becomes bigger.

Since a mixture of unreacted propylene, propylene oxide and cumyl alcohol as a reaction mixture is obtained in the epoxidation step, unreacted propylene is separated, subsequently a liquid containing propylene oxide and cumyl alcohol is subjected to separation. A liquid containing cumyl alcohol obtained here is used as a raw material, cumyl alcohol contained in the raw material is converted into α-methylstyrene with activated alumina as a dehydration catalyst, and the concentration of propylene oxide in the raw material is controlled to 0 to 10,000 ppm by weight, preferably 0 to 5,000 ppm by weight by applying the present invention. Rectification can make the propylene oxide concentration within the above-range, and the rectification can be easily carried out by properly determining rectification conditions such as a theoretical plate number of a rectification column used and the like.

As mentioned above, α-methylstyrene is obtained by dehydration of cumyl alcohol in the dehydration step, and, in this dehydration step, it is possible to use, as an inert gas, hydrogen to be used in the next hydrogenation step.

As the hydrogenation catalyst used in the hydrogenation step, a catalyst containing a metal of Group 10 or 11 of the Periodic Table, can be listed. Specifically, nickel, palladium, platinum and copper are listed, and among these, palladium and copper are preferable from viewpoints of suppression of hydrogenation of the aromatic ring and high yield. A copper-based catalyst includes copper, Raney copper, copper-chromium, copper-zinc, copper-chromium-zinc, copper-silica, copper-alumina and the like. A palladium-based catalyst includes palladium-alumina, palladium-silica, palladium-carbon and the like. These catalysts can be used alone or in plural kinds.

Preferable embodiments of the hydrogenation are as follows:

The hydrogenation is usually carried out by contacting α-methylstyrene and hydrogen with the hydrogenation catalyst, and when the hydrogenation is carried out subsequent to the dehydration as described above, water generated in the dehydration is also fed to the hydrogenation catalyst. The reaction can be carried out in a liquid phase using a solvent or a gas phase. The solvent should be substantially inert to the reactants and products. The solvent may be a substance existing in an α-methylstyrene solution to be used. For example, when α-methylstyrene is a mixture with cumene as a product, it is possible to use cumene as a substitute of the solvent without adding a solvent in particular. As other useful solvents, there can be listed alkanes (e.g. octane, decane, dodecane), mono-cyclic aromatic compounds (e.g. benzene, ethylbenzene, toluene) and the like. The hydrogenation temperature is usually 0 to 500° C., and preferably 30 to 400° C. In usual, the pressure is advantageously 100 to 10,000 kPa.

The above-described dehydration and hydrogenation can be advantageously conducted by a continuous method using a catalyst in the form of a fixed bed. As a reactor used for a continuous method, though there are an adiabatic reactor and isothermal reactor, the adiabatic reactor is preferred because the isothermal reactor requires a device for heat removal. In a case of the adiabatic reactor, the temperature lowers with progress of the reaction because the dehydration of cumyl alcohol is an endothermic reaction, and, on the other hand, since the hydrogenation of α-methylstyrene is an exothermic reaction, the temperature rises with progress of the reaction. The outlet temperature becomes higher than the inlet temperature because the generated heat quantity is larger in total.

The reaction temperature and pressure are selected so that water in the solution is not condensed. The reaction temperature is preferably 150 to 300° C., and the reaction pressure is preferably 100 to 2,000 kPa. When the temperature is too low or the pressure is too high, water is condensed leading to deterioration of the performance of the hydrogenation catalyst. Further, when the pressure is too high, it is also disadvantageous in the reaction equilibrium of dehydration. When the temperature is too high or the pressure is too low, it may become disadvantageous because the catalyst life is shortened by howling or the like caused by much generation of the gas phase part.

Hydrogen can be supplied from any one of inlets of a dehydration catalyst zone and inlets of a hydrogenation catalyst zone of a fixed bed reactor, and it is preferable to supply from the inlet of the dehydration catalyst zone of the fixed-bed reactor in view of the activity of the dehydration catalyst. That is, vaporization of water produced through dehydration is promoted by bringing into constant existence of hydrogen in the dehydration zone and the equilibrium dehydration conversion rises, therefore, high conversion can be attained effectively compared to absence of hydrogen.

Though water generated in the dehydration is passed through the hydrogenation catalyst, it is possible to operate at low cost without particularly setting up an apparatus for water removal as described above, by operating at the level not condensing water. Further, unreacted hydrogen from the outlet of the reactor can be recycled and used after a gas-liquid separation operation. Furthermore, at the time of the gas-liquid separation operation, it is possible to separate water generated in the dehydration from the reaction mixture. A part of the obtained reaction mixture (mainly cumene) can be recycled to the inlet of the reactor for use.

The amount of the dehydration catalyst may be an amount so that cumyl alcohol is sufficiently converted, and the conversion of cumyl alcohol is preferably 90% or more. The amount of the hydrogenation catalyst may be an amount so that α-methylstyrene is sufficiently converted, and the conversion of α-methylstyrene is preferably 98% or more.

Considering from a viewpoint of cost, the dehydration and hydrogenation catalysts are preferably packed in one reactor without using multi stage reactor.

Inside of the reactor may be partitioned into several beds or not. When the reactor is not partitioned, the dehydration catalyst and hydrogenation catalyst may be directly contacted each other or those may be partitioned with an inert packing.

EXAMPLE

Next, the present invention is explained in more detail by Examples.

Example 1

A cumene solution (containing 0 ppm by weight of propylene oxide) containing 25% by weight of cumyl alcohol and hydrogen were passed through a fixed bed flow reactor in which activated alumina was packed, at a rate of 1.6 g/minute and 105 Ncc/minute, respectively. In addition, LHSV(Liquid Hourly Space Velocity) was 9 $h^{-1}$, the pressure was 1.0 MPaG, and the temperature was 200° C. The dehydration conversion of cumyl alcohol in the obtained reaction mixture was 97%.

Example 2

It was carried out in the same manner as in Example 1 except that a cumene solution (containing 110 ppm by weight of propylene oxide) containing 25% by weight of cumyl alcohol was used. The dehydration conversion of cumyl alcohol in the obtained reaction mixture was 97%.

Example 3

It was carried out in the same manner as in Example 1 except that a cumene solution (containing 1200 ppm by weight of propylene oxide) containing 25% by weight of cumyl alcohol was used. The dehydration conversion of cumyl alcohol in the obtained reaction mixture was 96%.

Comparative Example 1

It was carried out in the same manner as in Example 1 except that a cumene solution (containing 12500 ppm by weight of propylene oxide) containing 25% by weight of cumyl alcohol was used. The dehydration conversion of cumyl alcohol in the obtained reaction mixture was 68%.

INDUSTRIAL APPLICABILITY

According to the present invention, there can be provided a process for producing α-methylstyrene, which can attain efficiently high conversion of cumyl alcohol at low cost.

The invention claimed is:

1. A process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene;

dehydration step: a step of obtaining α-methylstyrene by dehydrating cumyl alcohol obtained in the epoxidation step in the presence of activated alumina wherein a concentration of propylene oxide in cumyl alcohol is 0 to 10,000 ppm by weight; and hydrogenation step: a step of hydrogenating α-methylstyrene in the presence of a hydrogenation catalyst to convert into cumene and recycling said cumene to the oxidation step.

2. The process according to claim 1, wherein the concentration of propylene oxide is 0 to 5,000 ppm by weight.

* * * * *